United States Patent [19]
Pannetier et al.

[11] Patent Number: 5,747,246
[45] Date of Patent: May 5, 1998

[54] PROCESS FOR DETERMINING THE QUANTITY OF A DNA FRAGMENT OF INTEREST BY A METHOD OF ENZYMATIC AMPLIFICATION OF DNA

[75] Inventors: Christophe Pannetier, Paris; Madeleine Cochet, Fontenay-Aux-Roses; Sylvie Darche, Brunoy; Philippe Kourilsky, Paris, all of France

[73] Assignees: Institute National de la Sante et de la Recherche Medicale (INSERM), Paris; Institut Pasteur, Paris Cedex, both of France

[21] Appl. No.: 263,413

[22] Filed: Jun. 21, 1994

Related U.S. Application Data

[63] Continuation of Ser. No. 882,980, May 14, 1992, abandoned.

[30] Foreign Application Priority Data

Nov. 15, 1991 [FR] France ............................... 91 14089

[51] Int. Cl.$^6$ ....................................................... C12Q 1/68
[52] U.S. Cl. ................................................. 435/6; 435/912
[58] Field of Search ......................................... 435/6, 91.2

[56] References Cited

U.S. PATENT DOCUMENTS 5,082,935  1/1992  Cruickshank ........................... 536/27

FOREIGN PATENT DOCUMENTS

WO 91/02817  3/1991  WIPO .

OTHER PUBLICATIONS

Kemp et al. Colorimetric Detection of Specific DNA Segments Amplified by Polymerase Chain Reactions. Proc. Natl. Acad. Sci. USA (Apr. 1989) 86:2423–2427.

Konat, G. et al. Generation of Radioactive and Nonradioactive ssDNA Hybridization Probes by Polymerase Chain Reaction. Technique (1991) 3:64–68.

Norval, M., et al. Advances in the Use of Nucleic Acid Probes in Diagnosis of Viral Diseases of Man Brief Review. Arch. V.201 (1987) 97:151–165. (Abstract).

Nucleic Acids Research, vol. 17, No. 22, 1989, pp. 9437–9446, M. Becker–Andre, et al., "Absolute mRNA Quantification Using the Polymerase Chain Reaction (PCR). A Novel Approach by a PCR Aided Transcript Titration Assay (PATTY)".

Proceedings of the National Academy of Sciences of USA, vol. 87, Apr. 1990, pp. 2725–2729, G. Gilliland, et al., "Analysis of Cytokine mRNA and DNA: Detection and Quantitation by Competitive Polymerase Chain Reaction".

*Primary Examiner*—Scott W. Houtteman
*Attorney, Agent, or Firm*—Oblon, Spivak, McClelland, Maier & Neustadt, P.C.

[57] ABSTRACT

The present invention relates to a process for determining the quantity of a DNA fragment of interest in a sample wherein:

1) a standard DNA fragment can be amplified with the same oligonucleotide primers is added to the sample to be analyzed containing the DNA fragment of interest, the standard DNA fragment and the fragment of interest differing in sequence and/or in size by not more than 10%, 2) the DNA fragment of interest and the standard fragment are coamplified with the same primers, preferably to saturation of the amplification of the DNA fragment of interest, 3) one or more labeled oligonucleotide primer(s), specific for the DNA fragment of interest and the standard fragment and different from the primers of step 2), is/are added to the reaction medium obtained in step 2), so that, after denaturation of the DNA, said primer(s) hybridize(s) with said fragments at a suitable site in order that an elongation with the DNA polymerase generates labeled DNA fragments of different sizes and/or sequences or with different labels according to whether they originate from the DNA fragment of interest or the standard fragment, respectively, and then 4) the initial quantity of DNA fragment of interest is determined as being the product of the initial quantity of standard DNA fragment and the ratio of the quantity of amplified DNA fragment of interest to the quantity of amplified standard DNA fragment.

27 Claims, 10 Drawing Sheets

| | |
|---|---|
| H2-I | CTGACCT GGCAGTTGAA |
| H2-III | |
| pH-2 | ...GCCCTGG GCTTCTACCC TGCTGATATC ACCCTGACCT GGCAGTTGAA |
| pH-2-stand | ...GCCCTGG GCTTCTACCC TGCTGATATC ACCCTGACCT GGCAGTTGAA |
| H2-II | |
| | |
| H2-I | TGG |
| H2-III | |
| pH-2 | TGGGGAGGAC CTGACCCAGG ACATGGAGCT TGTAGAGACC AGGCCTGCAG |
| pH-2-stand | TGGGGAGGAC CTGACCCAGG ACATGGAGCT TGTAGAGACC AGGCCTGCAG |
| H2-II | |
| | |
| H2-I | |
| H2-III | XCTG TGGTGGTGCC TCTTGG |
| pH-2 | GGGATGGAAC CTTCCAGAAG TGGGCAGCTG TGGTGGTGCC TCTTGGGAAG |
| pH-2-stand | GGGATGGAAC CTTCCAGAAG TGGGCAGCTG TGGTGGTGCC TCTTGGGAAG |
| H2-II | |
| | |
| H2-I | |
| H2-III | |
| pH-2 | GAGCAGAATT ACACATGCCA TGTGCACCAT AAGGGGCTGC CTGAGCCTCT |
| pH-2-stand | GAGCAGAATT ACACATGCCA TGTGCACCAT AAGGGGCTGC CTGAGCCTCT |
| H2-II | |
| | |
| H2-I | |
| H2-III | |
| pH-2 | CACCCTGAGA TGGA----AG CTTCCTCCAT CCACTGTCTC CAACACGGTA |
| pH-2-stand | CACCCTGAGA TGGAAGCTAG CTTCCTCCAT CCACTGTCTC CAACACGGTA |
| H2-II | |
| | |
| H2-I | |
| H2-III | |
| pH-2 | ATCATTGCTG TTCTGGTTGT CCTTGGAGCT GCAATAGTCA CTGGAGCTGT |
| pH-2-stand | ATCATTGCTG TTCTGGTTGT CCTTGGAGCT GCAATAGTCA CTGGAGCTGT |
| H2-II | GGAACCTCGA CGTTATCAGT |
| | |
| H2-I | |
| H2-III | |
| pH-2 | ... |
| pH-2-stand | ... |
| H2-II | |

*FIG. 1*

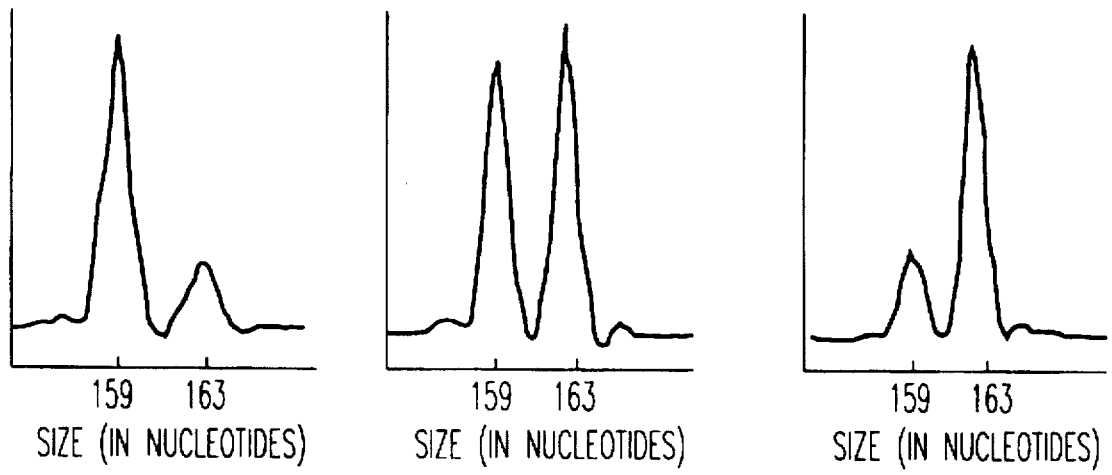
FIG.2A(1)   FIG.2A(2)   FIG.2A(3)
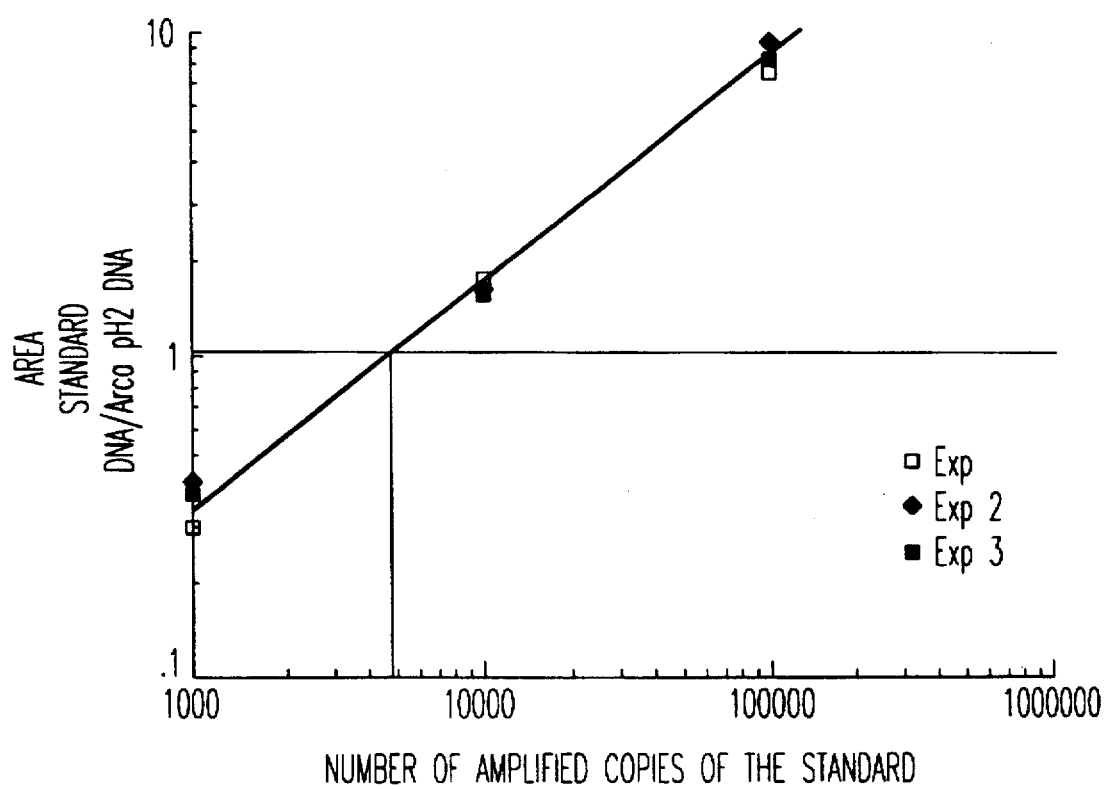
FIG.2B

```
V primer                   CTGAATG CCCAGACAGC TCCAAGC
                           ....... .......... .......
                           ....... .......... .......
EWS147      AGTCGTTTTA TACCTGAATG CCCAGACAGC TCCAAGCTAC TTTTACATAT
            .......... .......... .......... .......... ..........
            .......... .......... .......... .......... ..........
K17         AGTCGTTTTA TACCTGAATG CCCAGACAGC TCCAAGCTAC TTTTACATAT ATCTGCCGTG GATCCAGAAG ACTCAGCTGT CTATTTTTGT GCCAGCAGCC
            .......... .......... .......... .......... ..........
            .......... .......... .......... .......... ..........
            ATCTGCCGTG GATCCAGAAG ACTCAGCTGT CTATTTTTGT GCCAGCAGCC AGATAACTAG TAACCAAGAC ACCCAGTACT TTGGGCCAGG CACTCGGCTC
            .. ... .   .... . .......... .......... ..........
            A-ACGACTGG GGG---AGAC A-CCAGTACT TTGGGCCAGG CACTCGGCTC
                                  .......... .......... ...
                                  .......... .......... ...
J primer                          CCAGTACT TTGGGCCAGG CAC CTCGTGTAGA GGATCTGAGA AATGTGACTC CACCCAAGG
            .......... .......... .......... .........
            .......... .......... .......... .........
            CTCGTGTAGA GGATCTGAGA AATGTGACTC CACCCAAGG
                                  .... .......... ........
C primer                          GAGA AATGTGACTC CACCCAAG
```

FIG. 5

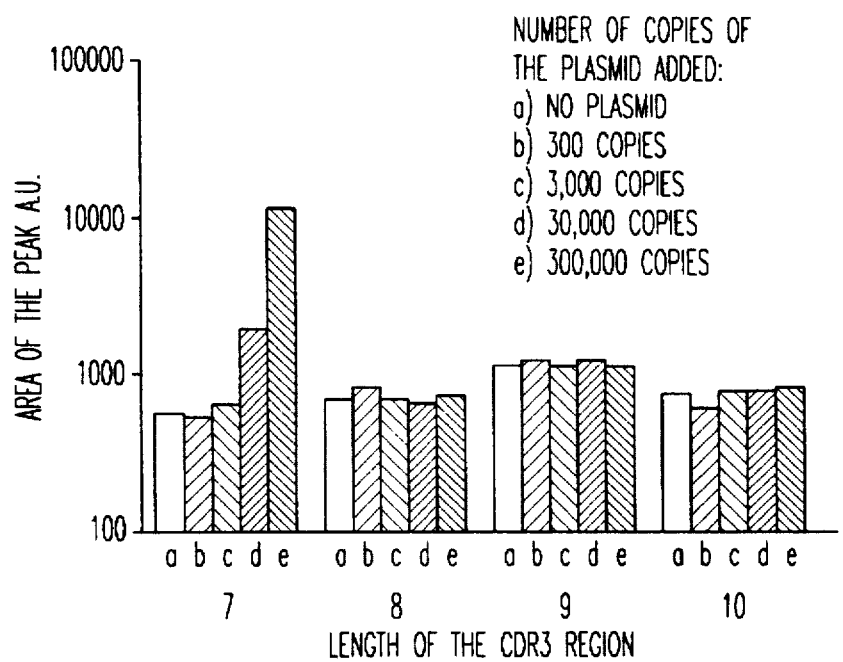

FIG. 6

```
Ald-1                                                     GACCCAC CCCGTCCTGT
                                                          ........ ..........
Aldolase H      AGTCCTTTCG CCTACCCACC CGCGTACCAG GCAGACCCAC CCCGTCCTGT
                .......... .......... .......... .......... ..........
Standard DNA    AGTCCTTTCG CCTACCCACC CGCGTACCAG GCAGACCCAC CCCGTCCTGT GCC
                ...
                GCCAGGAAAG CAACTGCCAC CGGCACCATG CCCCACCCAT ACCCAGCACT
                .......... .......... .....      .......... ..........
                GCCAGGAAAG CAACTGCCAC CGGCAC---- CCCCACCCAT ACCCAGCACT GACCCCGGAG CAGAAGAAGG AGCTGTCTGA CATCGCTCAC CGCATTGTGG
                .......... .......... .......... .......... ..........
                GACCCCGGAG CAGAAGAAGG AGCTGTCTGA CATCGCTCAC CGCATTGTGG
                                         .. .......... .......... .
Ald-III                                  GG AGCTGTCTGA CATCGCTCAC C CTCCGGGCAA GGGCATCCTG GCTGCAGATG AGTCCACCGG AAGCATTGCC
                .......... .......... .......... .......... ..........
                CTCCGGGCAA GGGCATCCTG GCTGCAGATG AGTCCACCGG AAGCATTGCC AAGCGCCTGC AGTCCATTGG CACCGAGAAC ACCGAGGAGA ACAGGCGCTT
                .......... .......... .......... .......... ..........
                AAGCGCCTGC AGTCCATTGG CACCGAGAAC ACCGAGGAGA ACAGGCGCTT CTACCGCCAG CTGCTGCTGA CTGCAGACGA CCGTGTGAAT CCCTGCATTG
                .......... .......... .......... .......... ..........
                CTACCGCCAG CTGCTGCTGA CTGCAGACGA CCGTGTGAAT CCCTGCATTG GGGGGGTGAT CCTCTTCCAC GAGACACTGT ACCAGAAGGC AGATGATGGA
                .......... .......... .......... .......... ..........
                GGGGGGTGAT CCTCTTCCAC GAGACACTGT ACCAGAAGGC AGATGATGGA
                .......... .......... ...
Ald-II             GGGTGAT CCTCTTCCAC GAG Ubi-I                                             GACGGGCA AGACCATCAC
                                                  ........ ..........
Ubiquitin       CGCGCCAACA TGCAGATCTT CGTGAAGACC CTGACGGGCA AGACCATCAC
                .......... .......... .......... .......... ..........
Standard DNA    CGCGCCAACA TGCAGATCTT CGTGAAGACC CTGACGGGCA AGACCATCAC TCTTGAGGTC GAGCCCAGTG ACACCATCGA GAATGTCAAG GCCAAGATCC
                .......... .......... .......... .......... ..........
                TCTTGAGGTC GAGCCCAGTG ACACCATCGA GAATGTCAAG GCCAAGATCC
                ..
                TC
```

*FIG. 7A*

```
                    AAGACAAGGA AGGCATCCCA CCTGACCAGC AGAGGCTGAT ATTCGCGGGC
                    .......... .......... .......... .......... ..........
                    .......... .......... .......... .......... ..........
                    AAGACAAGGA AGGCATCCCA CCTGACCAGC AGAGGCTGAT ATTCGCGGGC

Ubi-III               GG AGGATGGCCG CACCCTGTCC
                           .. .......... ..........
                           .. .......... ..........
                    AAACAGCTGG AGGATGGCCG CACCCTGTCC GACTACAACA TCCAGAAAGA
                    .......... .......... .......... .......... ..........
                    .......... .......... .......... .......... ..........
                    AAACAGCTGG AGGATGGCCG CACCCTGTCC GACTACAACA TCCAGAAAGA

GTCCACCTTG CACCTGGTGC TGCGTCTGCG CGGTGGCATC ATTGAGCCAT
                    .......... .......... ...... ... .......... ..........
                    .......... .......... .......... ..........
                    GTCCACCTTG CACCTGGTGC ----TCTGCG CGGTGGCATC ATTGAGCCAT

CCCTTCGTCA GCTTGCCCAG AAGTACAACT GTGACAAGAT GA
                    .......... .......... .......... .......... ..
                    .......... .......... .......... .......... ..
                    CCCTTCGTCA GCTTGCCCAG AAGTACAACT GTGACAAGAT GA
                                          .......... ..........
     Ubi-II                 GCTTGCCCAG AAGTACAACT

PIA-I                          A ACAAGAAACC AGACAAAGCC
                                    . .......... ..........
                                    . .......... ..........
     PIA            CCTTTGTGCC ATGTCTGATA ACAAGAAACC AGACAAAGCC CACAGTGGCT
                    .......... .......... .......... .......... ..........
                    .......... .......... .......... .......... ..........
     Standard DNA   CCTTTGTGCC ATGTCTGATA ACAAGAAACC AGACAAAGCC CACAGTGGCT CAGGTGGTGA CGGTGATGGG AATAGGTGCA ATTTATTGCA CCGGTACTCC
                    .......... .......... .......... .......... ..........
                    .......... .......... .......... .......... ..........
                    CAGGTGGTGA CGGTGATGGG AATAGGTGCA ATTTATTGCA CCGGTACTCC CTGGAAGAAA TTCTGCCTTA TCTAGGGTGG CTGGTCTTCG CTGTTGTCAC
                    .......... .......... .......... .......... ..........
                    .......... .......... .......... .......... ..........
                    CTGGAAGAAA TTCTGCCTTA TCTAGGGTGG CTGGTCTTCG CTGTTGTCAC
                                                              .. ..........
     PIA-III                                                 CG CTGTTGTCAC AACAAGTTTT CTGGCGCTCC AGATGTTCAT AGACGCCCTT TATGAGGAGC
                    .......... .......... .......... .......... ..........
                    .......... .......... .......... .......... ..........
                    AACAAGTTTT CTGGCGCTCC AGATGTTCAT AGACGCCCTT TATGAGGAGC
                    .......... .....
                    AACAAGTTTT CTGGC AGTATGAAAG GGATGTGGCC TGGATAGCCA GGCAAAGCAA GCGCATGTCC
                    .......... .......... .......... .......... ..........
                    .......... .......... .......... .......... ..........
                    AGTATGAAAG GGATGTGGCC TGGATAGCCA GGCAAAGCAA GCGCATGTCC TCTGTCGATG AGGATGAAGA CGATGAGGAT GATGAGGATG ACTACTACGA
                    .......... .......... .......... .......... ..........
     FIG. 7B        TCTGTCGATG AGGATGAAGA CGATGAGGAT GATGAGGATG ACTACTACGA
```

```
CGACGAGGAC GACGACGACG ATGCCTTCTA TGATGATGAG GATGATGAGG
.......... .......... .......... .......... ..........
.......... .......... .......... .......... ..........
CGACGAGGAC GACGACGACG ATGCCTTCTA TGATGATGAG GATGATGAGG

AAGAAGAATT GGAGAACCTG ATGGATGATG AATCAGAAGA TGAGGCCGAA
.......... .......... .......... .......... ..........
.......... .......... .......... .......... ..........
AAGAAGAATT GGAGAACCTG ATGGATGATG AATCAGAAGA TGAGGCCGAA

GAAGAGATGA GCGTGGAAAT GGGTGCCGGA GCTGAGGAAA TGGGTGCTGG
.......... .......... .......... .......... ..........
.......... .......... .......... .......... ..........
GAAGAGATGA GCGTGGAAAT GGGTGCCGGA GCTGAGGAAA TGGGTGCTGG
                                            ..........
                                            ..........
P1A-11                                       GGTGCTGG

CGCTAACTGT GCCTGTGTTC CTGGCCATCA TTTAAGGAAG AATGAAGTGA
.......... .......... .......... .......... ..........
.......... .......... .......... .......... ..........
CGCTAACTGT GCCTGTGTTC CTGGCCATCA TTTAAGGAAG AATGAAGTGA
.......... .
.......... .
CGCTAACTGT G
```

*FIG. 7C*

```
    ↓
GTTGAC
||||||
CAACTG
```

```
GTTGAC ─────────────
C AsAsC T G ─────────────
```

```
     ↓
G T T G A C ─────────────
C AsAsC T G ─────────────
```

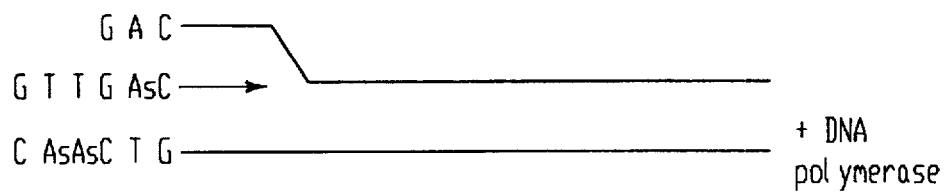
FIG. 8e
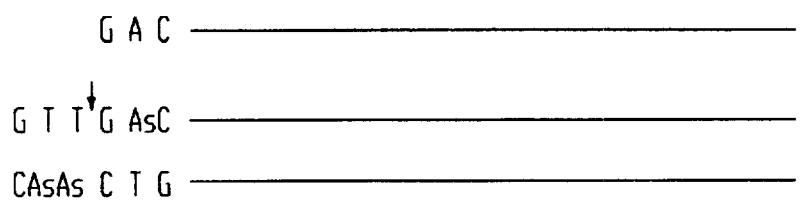
FIG. 8f
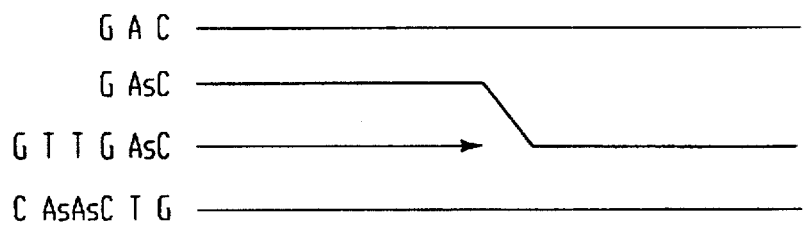
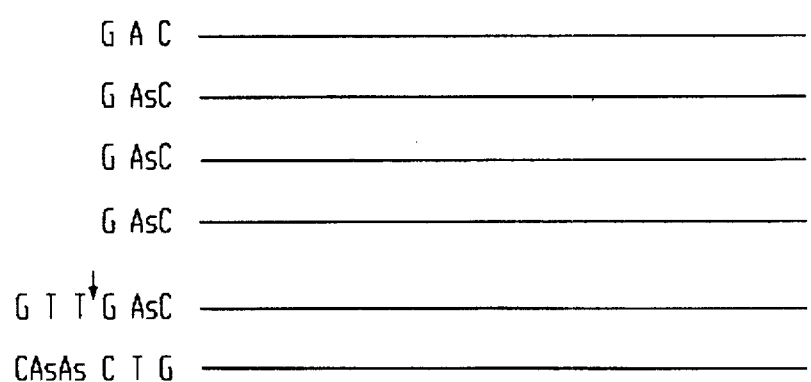
FIG. 8g

PROCESS FOR DETERMINING THE QUANTITY OF A DNA FRAGMENT OF INTEREST BY A METHOD OF ENZYMATIC AMPLIFICATION OF DNA

This application is a Continuation of application Ser. No. 07/882,980, filed on May 14, 1992, now abandoned.

BACKGROUND OF THE INVENTION

1. Field of the Invention

The present invention relates to methods of enzymatic amplification in vitro of single-stranded or double-stranded DNA nucleic acid sequences, in particular by PCR (polymerase chain reaction) or by the SDA (strand displacement amplification) technique. More specifically, the present invention relates to an improvement of these amplification methods, enabling the initial sequence of interest to be quantified after amplification.

2. Discussion of the Background

Techniques of enzymatic amplification of DNA are well known to persons skilled in the art.

In vitro amplification techniques, in particular by PCR or SDA, have been described in the literature, and their use and improvements to them have been the subject of patent applications. The European Publications EP 201,184 and EP 200,362 on the basic technique for the PCR method may be mentioned in particular. The so-called SDA (strand displacement amplification) amplification technique was described at the San Diego Conference on Nucleic Acids held on Nov. 20–22, 1991.

In these methods of enzymatic amplification of DNA, amplification of the sequence is accomplished in successive cycles. One cycle entails several steps: a first step of thermal denaturation of the DNA, which separates, where appropriate, double-stranded DNA into two single strands, a second step of hybridization of primers with the 5' ends of the sequences of the single strands which are complementary to them, and a third step of elongation from the 3' ends of the primers using a DNA polymerase. Specific oligonucleotide primers are used, which will hybridize with sequences which are complementary to them flanking at its 5'-P ends the DNA fragment to be amplified. The 3'-OH ends of these primers constitute the starting point for an elongation performed, in the 5'→3' direction, by DNA replicating enzymes known as DNA polymerases.

For an amplification, the reaction medium hence contains the DNA to be amplified, primers, DNA polymerase and also other components such as a buffer, salts and deoxynucleotide triphosphates. Each strand of the fragment then serves as a template for the enzyme which synthesizes the complementary strands; the multiplication factor is then two. The oligonucleotide "primers" are rehybridized again with the DNA strands originating from the first amplification cycle, each strand serving as a template for the DNA polymerase. The amplification factor will then be four—and so on—with theoretical doubling of the copies of the DNA fragment in each cycle.

In some techniques of enzymatic amplification of DNA, such as the PCR technique, the products emanating from this first cycle, and then from each successive cycle, are heat denatured. The use of a heat-stable polymerase, Taq polymerase, has enabled automatic cyclers (hybridization/enzymatic polymerization/thermal denaturation) to be developed, making routine use of the method easier. The operating conditions of the various steps differ, in effect, essentially in the temperature at which they take place. The denaturation conditions generally correspond to a rise in the temperature of the reaction medium above 90° C., hybridization generally takes place at between 50° and 70° C. and elongation with DNA polymerase may be accomplished at relatively high temperatures, of the order of 70° C., if a heat-stable DNA polymerase is used.

In contrast, in other techniques of enzymatic amplification of DNA, such as the SDA technique, the products emanating from the first cycle, and from each successive cycle, are not denatured. These methods are isothermal.

The SDA amplification method is based on the use of oligonucleotide primers modified at the 5' end by the addition of a DNA sequence recognized by a restriction enzyme, for example the enzyme Hinc II. The process requires the formation of a thiolated restriction site by incorporation of sulfur-containing deoxyadenosine triphosphate (hereinafter designated ATPs), and the alternate actions of said enzyme Hinc II which partially hydrolyzes (on only one strand) said restriction site, and of DNA polymerase which synthesizes a new strand from the point of hydrolysis, with simultaneous displacement of the previously cut nucleic acid sequence without denaturation being necessary. Hybridization of the modified primers with the target necessitates only a first step of denaturation of the DNA. The reaction then takes place at 37° C. The method permits an average amplification of the target of the order of $10^7$.

The medium comprises the following reactants:
+dTTP, dGTP, dCTP and dATP
+DNA polymerase
+Target DNA to be amplified
+the enzyme Hinc II. A sequence recognized by the enzyme Hinc II is shown in FIG. 8a.

The arrow indicates the cleavage site.

The primer modified at the 5' end by coupling to the sequence GTTGAC is recognized by the enzyme Hinc II.

Starting from one of the single strands resulting from the initial denaturation of the DNA to be amplified, an illustrative amplification scheme is as follows:

(1) Hybridization of the primer with the complementary strand (see FIG. 8b):

(2) Synthesis of the complementary strand with DNA polymerase:

The incorporation of dATPs leads to the formation of a thiolated restriction site which is incompletely recognized by Hinc II and is hence not cleaved (see FIG. 8c)

(3) Partial hydrolysis of the restriction site with Hinc II: Cleavage takes place only on the unthiolated strand (see FIG. 8d).

(4) Synthesis of the DNA strand with DNA polymerase: The polymerase becomes "anchored" to the hydrolyzed site (FIG. 8e).

It resynthesizes a strand corresponding to the cut strand, displacing the latter as the synthesis proceeds (FIG. 8f).

(5) Further actions of Hinc II and of DNA polymerase, leading to further syntheses with displacement of hydrolyzed strands (FIG. 8g).

G A C
G AsC

Reaction takes place simultaneously on both strands of target DNA, leading to an exponential increase in the number of copies as a function of the reaction time.

An amplification by a factor of $10^7$ may be obtained in 2 hours at 37° C.

In all the amplification methods, theoretically, after a first cycle, a sequence of interest to be amplified, present in $y_o$ copies in the test sample, will be duplicated to $2 y_o$ copies. After n amplification cycles, the number of target sequences will be multiplied by $2^n$, that is to say a target sequence present initially in $y_o$ copies will be present in $y=y_o \cdot 2^n$ copies. However, experimental efficiencies are not 100% in each cycle. The efficiency or yield of the reaction "eff" during a cycle is not 100%; instead, the value of the number of sequences of: $y=Y_o \cdot (1+\text{eff})^n$ [sic] is obtained rather than $\times 2^n$, with eff<1.

One of the difficulties of the methods of enzymatic amplification of DNA is, in effect, to obtain a quantitative reaction, that is to say to be able to quantify accurately the quantity of DNA in a sample, or the relative values of two DNA fragments in a given sample.

To overcome this problem, several methods have been envisaged (Wang et al., 1989, Gilliland, 1990). They all share the following common features:

a) an internal calibration is performed using standard samples of nucleic acids of known concentrations and which can be amplified with the same oligonucleotide primers as those used to amplify the sequences of interest, and b) a coamplification of the sequences of interest and standard sequences is carried out and the amplification reactions are stopped at intervals of two or three cycles, after a relatively small number of cycles, that is to say while the amplification is in an exponential phase and before saturation of the amplification or in a stationary phase, and then c) the amplification products are separated into amplified standard DNA sequences and amplified DNA sequences of interest, according to their size, by known techniques such as gel electrophoresis, and the quantity of initial DNA sequence of interest may be determined by known means from the initial quantity of standard sequences and the ratio of the quantities of amplified standard sequences and amplified sequences of interest, it being considered that the ratio of the quantities of the initial and amplified sequences is identical.

In a previous technique (Singer-Sam, et al., 1990 and Robinson and Simon, 1991), the method consisted, while varying the number of amplification cycles, in measuring the yields (Y) every two or three cycles while the amplification reaction takes place in its exponential phase. The yield (Y) then obeys the equation $Y=Y_o (1+\text{eff})^n$ where n is the number of cycles and eff the efficiency of the reaction in a cycle.

However, it has been discovered that it is not possible to perform a prior calibration, before the analysis to be performed, but that it is necessary to make use of an internal standard during the analysis and the amplification if an accurate quantification is desired, this probably being due to the very large number of parameters involved in the amplification and the great variability of their natures which influence the yield of the amplification and hence its quantification.

In the methods of enzymatic amplification of DNA, after a certain number of cycles, a saturation phase or stationary phase occurs with the appearance of a plateau, the specific amplification products (sequences of interest and standard sequences) no longer being amplified. In effect, at this point, provided there is a sufficient quantity of the DNA polymerase enzyme, the amplification products are present in large numbers and compete with the primers which, for their part, are in smaller quantities, and shift the equilibrium towards a hybridization of the specific amplification products with one another rather than with the primers.

The number of cycles after which this saturation phase appears varies in accordance with the initial quantity of the product to be amplified and the quantities and efficiency of the reactants used (primers and polymerases in particular) in the amplification reaction.

However, under normal conditions of carrying out amplification, this number of cycles will be approximately 40.

In the previous technique mentioned above, it is absolutely essential to avoid performing quantification measurements once saturation has been reached or in the last cycles before saturation. In effect, this saturation of the amplification of the specific sequences leads to an increase in the background due to the amplification of non-specific products which, for their part, continue to be amplified exponentially. These non-specific amplification products correspond to sequences possessing a sequence homology with the sequence of interest, so that they are amplified by the same primers; their amplification begins to occur essentially in the last cycles before the stationary phase.

It was hence necessary, before the invention, to make several measurements at regular intervals, every two or three amplification cycles as mentioned above, to verify that the measurement taken into account has indeed been performed at a sufficiently advanced stage but nevertheless a sufficiently long time before saturation, inasmuch as the amplification of non-specific sequences begins a few cycles before the stationary phase. This is a very considerable practical constraint.

Another major practical problem of this previous technique is that significant variations in amplification are observed from tube to tube during the exponential phase, especially because the efficiency of the PCR is, during this phase, highly variable. This reduces the accuracy of the measurements and makes them sample-dependent. This is a major drawback if it is desired to perform and compare, as is the case in practice, several analyses in parallel on samples of diverse origins.

In the prior art, the relative quantification of amplified DNA fragments of interest and standard fragments may be done:

either by using a labeled primer during the amplification, or, after amplification, by gel hybridization with labeled DNA probes, enabling the DNA fragments of interest and standard fragments to be distinguished, which nevertheless involves DNA fragments of interest and standard fragments of sufficiently different size.

In both cases, the DNA fragments of interest and standard fragments are separated according to their size by gel electrophoresis, and the intensity of the signal corresponding to the label then permits a relative quantification of the amplified DNA fragments of interest and standard fragments.

SUMMARY OF THE INVENTION

The aim of the present invention is to provide a method of quantification of a DNA fragment by a method of enzymatic amplification which is easier to carry out, more accurate, more reliable and reproducible from sample to sample.

To this end, the subject of the present invention is a process for determining the quantity of a DNA fragment of interest in a sample to be analyzed by a method of enzymatic amplification in vitro of said fragment, characterized in that:

1) a specified quantity of a standard DNA fragment which differs from the DNA fragment of interest but can be amplified with the same oligonucleotide primers is added to the sample to be analyzed containing the DNA fragment of interest, the standard DNA fragment and the fragment of interest being as similar as possible and differing in sequence and/or in size by not more than 10% of nucleotides, and preferably by not more than 5 nucleotides per strand, 2) the DNA fragment of interest and the standard fragment are coamplified with the same oligonucleotide primers, preferably to saturation of the amplification of the DNA fragment of interest or in the last cycles prior to saturation, 3) one or more labeled oligonucleotide primer(s), specific for the DNA fragment of interest and the standard fragment and different from the amplification oligonucleotide primers of step 2), is/are added to the reaction medium obtained in step 2), and one or more additional amplification cycle(s) with said primer(s) is/are performed with a DNA polymerase, so that, during a cycle, after denaturation of the DNA, said labeled oligonucleotide primer(s) hybridize(s) with said fragments at a suitable site in order that an elongation with the DNA polymerase generates labeled DNA fragments of different sizes and/or sequences and/or with different labels according to whether they originate from the DNA fragment of interest or the standard fragment, respectively, and then 4) the initial quantity of DNA fragment of interest is determined as being the product of the initial quantity of standard DNA fragment and the ratio of the quantity of amplified DNA fragment of interest to the quantity of amplified standard DNA fragment, which ratio is identical to that of the quantities of the labeled DNA fragments originating from the amplified DNA fragment of interest and the amplified standard fragment, respectively, obtained in step 3).

BRIEF DESCRIPTION OF THE DRAWINGS

FIGS. 1 to 4 illustrate Example 1 infra.

FIG. 1 shows the sequences of the 3' portion of the H-2 $K^d$ (PH-2) gene (class I gene) of the major histocompatibility complex (MHC), of the standard DNA (PH-$2_{stand}$), of the amplification primers (H2-I and H2-II) and of the third labeled primer (H.2-III).

FIG. 2a shows the resolution of the electrophoretic separation of two different amplified fragments, in variable initial concentrations.

FIG. 2b shows the curve for quantification of H-2 $K^d$ with the standard DNA.

FIG. 3 shows the curve for quantification of the cDNA transcripts of MHC class I genes in different organs.

FIG. 4 shows the increase in the MHC class I gene transcripts in a liver in acute phase.

FIG. 5 shows the cDNA sequences of the TcRbeta gene of BW5147 and of the clone K17.

FIG. 6 shows the results of Example 2.

FIG. 7 shows the sequences of the primers for DNA of interest and standard DNA of Example 4.

FIGS. 8a–g contain drawings corresponding to the SDA amplification scheme described above.

DETAILED DESCRIPTION OF THE PREFERRED EMBODIMENTS

Figure 3:
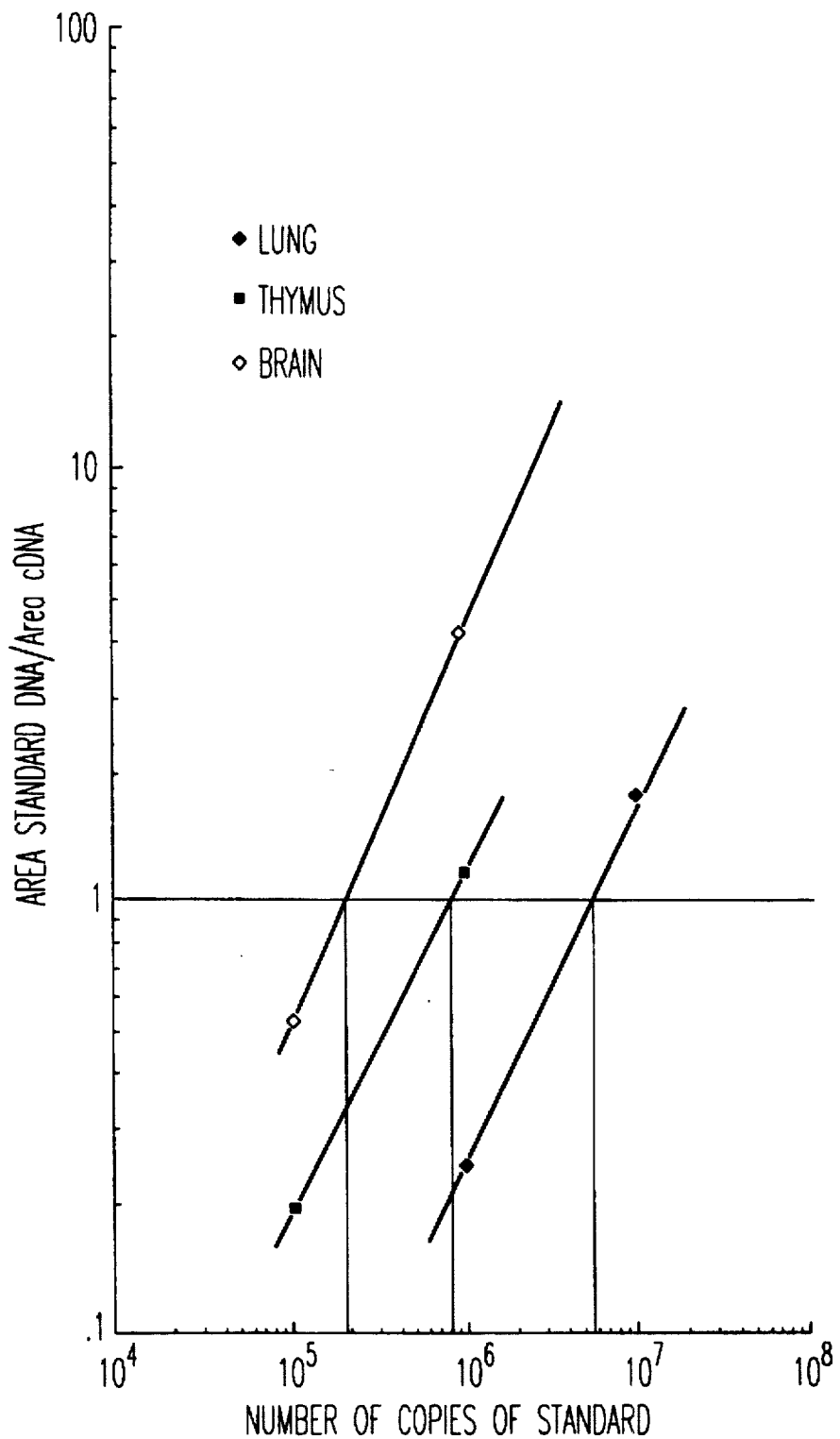

The specific elongation of the templates consisting of the amplification products (standard DNA and DNA of interest) in step 3), using primers which hybridize only with the latter products and partially recopy them, enables the non-specific amplification products to be removed inasmuch as only the specific products are henceforward labeled.

In step 3), only one additional amplification cycle or, at all events, a fairly small number, for example not more than 5, will preferably be performed so as to avoid the appearance of further background.

It will be noted that the standard DNA fragment and the fragment of interest necessarily have their ends identical, since they are amplified with the same primers during the amplification of step 2. Moreover, it will also be noted that the standard DNA fragment and the fragment of interest are of the same nature, namely single-stranded or double-stranded.

According to the invention, the DNA fragment of interest and the standard fragment are as similar in length and sequence as possible. Preferably, the standard fragment carries as minor a modification as possible relative to the DNA of interest, and differs in at least one site which can be identified by some appropriate means. This ensures a greater similarity in their level of amplification, which is a major factor for the accuracy and reliability of the method for reproduction from sample to sample.

In the present application, the expression "different in sequence" is understood to mean that a certain number of nucleotides of which the standard DNA fragment and the DNA fragment to be quantified are composed are different.

The DNA fragment to be quantified and the standard DNA fragment can have the same size, in which case one of the fragments will have to contain an "identifiable site", that is to say one enabling it to be distinguished from the other fragment by some means, in particular by specific cleavage of the fragment with a particular reagent such as a restriction enzyme.

However, in general, this difference in sequence is accompanied by a difference in size.

Preferably, the sizes of the DNA fragment of interest and the standard fragment differ by at least one nucleotide and by not more than approximately 10% of nucleotides per strand, or by 1 to 5 nucleotides.

In particular, it was discovered according to the invention that, irrespective of the reactant or the parameter which limits the amplification reaction, the amplification of the two molecules (DNA fragment of interest and standard DNA fragment) then proceeds in the same manner, even to saturation, so that the ratio of the respective quantities of the amplified DNA fragment of interest and the amplified standard DNA fragment remains identical to that of the starting molecules, which is not the case when the sequences of these two molecules differ more substantially.

When the DNA sequences of interest have between 50 and 500 base pairs (for double-stranded sequences) or nucleotides (for single-stranded sequences), the primers have approximately 15 to 25 nucleotides, so that, preferably, the difference in size and/or sequence between standard DNA fragments and DNA fragments of interest does not exceed 10%.

However, appropriately, when the size of the DNA fragment of interest is estimated at between 50 and 500 base pairs or nucleotides, the difference in size and/or sequence between the standard DNA fragment and the fragment of interest will be from two to five nucleotides.

For DNA sequences of interest of less than 50 base pairs, the differences in sequence and/or sizes between the DNA fragment of interest and the standard fragment are between one and five.

Appropriately, the difference in sequence of the standard DNA fragment may result from one or more deletion(s), mutation(s) or addition(s) of nucleotides in the DNA sequence of interest, carried out by conventional techniques of genetic engineering, the DNA sequence to be quantified and the standard sequence being in other respects identical.

In a particular embodiment of the invention, in step 3), a single third labeled oligonucleotide primer is added to the reaction medium obtained in step 2), the primer being common to the DNA fragment of interest and the standard fragment, and one or more additional amplification cycle(s) is/are performed with said third primer, so that, after denaturation of the DNA, said third primer hybridizes specifically with said fragments at a suitable site in order that an elongation with the DNA polymerase generates two types of labeled DNA fragments of different sizes according to whether they originate from the DNA fragment of interest or the standard fragment, respectively, and each containing only a portion of the latter fragments, respectively.

Most generally, the standard DNA fragment will differ from the DNA of interest at only one site, at which a mutation, deletion or addition of the chosen number of nucleotides, especially from 1 to 5 and preferably 3 to 4 nucleotides, will have been performed by known techniques of genetic engineering. In this case, said third primer hybridizes upstream from this site at which the two sequences diverge, so that, since the elongation takes place in the downstream direction (5'→3'), the DNA sequences labeled after elongation retain a difference in size according to whether they originate from the DNA fragment of interest or from the standard DNA fragment.

Another advantage of the method according to the present invention stems from the fact that, once saturation of amplification has been reached or at the end of the exponential phase, it is observed that there is no longer a difference in yield of the primers, and consequently in the amplification, from sample to sample, that is to say from tube to tube, which was seen in the exponential amplification phase in the prior art. At the plateau, a uniform state is reached, making the measurement according to the process of the invention accurate, reliable and reproducible from tube to tube, for this additional reason.

Another advantage of the method according to the invention results from its greater sensitivity in view of the fact that the products are amplified in greater copy number at saturation.

The fact that the DNA fragment of interest and the standard fragment are partially recopied in labeled form in step 3) enables them to be distinguished from the non-specific amplification products, although the latter are present in larger quantities in the saturation phase, since the non-specific products are unlabeled.

In another embodiment, the modifications which enable the standard DNA to be distinguished from the DNA to be quantified no longer concern the size, but concern the presence of a detectable modification such as a restriction site in one of them.

The subject of the present invention is hence also a process for determining the quantity of a DNA of interest, characterized in that:

a) the standard DNA fragment and the fragment of interest have the same size and differ in sequence by a restriction site for a particular endonuclease, or a site of cleavage which can be produced by any other means, and b) in step 3), a third labeled oligonucleotide primer is added to the reaction medium obtained in step 2), the primer being common to the DNA fragment of interest and the standard fragment, and one or more additional amplification cycle(s) is/are performed with said third oligonucleotide primer, so that, during a cycle, after denaturation of the DNA, said third primer hybridizes specifically with said fragments at a suitable site in order that an elongation with the DNA polymerase generates two types of labeled DNA fragments which differ according to whether they originate from the DNA fragment of interest or the standard fragment, respectively, in that one of said fragments still contains said restriction site, and c) before step 4), a digestion of the amplification products of step 3) is performed, using said endonuclease or any other means of cleavage corresponding to the cleavage site, so as to generate fragments of different sizes according to whether they originate from the DNA fragment of interest or the standard fragment.

The introduction or removal of an endonuclease restriction site may be done by directed mutagenesis or any other known method.

In a first embodiment, in step 4) of the process according to the invention, the measurement of the ratio of the quantities of standard DNA and DNA to be quantified requires the prior physical separation of these two species, it being possible for this separation to be done by gel electrophoresis or other methods known to persons skilled in the art.

Thus, appropriately, the determination in the last step according to the process of the invention is done by:
  separating the labeled DNA fragments originating from the amplified DNA fragment of interest and the amplified standard fragment according to their size by gel electrophoresis, and then by
  detecting the respective intensities of the signals corresponding to the label of said third primer for the labeled DNA fragments originating from the DNA fragment of interest and the standard fragment, respectively.

It will be advantageous to use "sequencer gels", consisting of devices for gel electrophoresis with DNA sequencing which enable sequences differing by only one nucleotide to be distinguished and separated.

As a label, conventional use may be made, in particular, of radioactive, enzymatic or fluorescent labeling, according to techniques well known to persons skilled in the art.

However, a fluorescent label will be the one used most especially, thereby enabling an altogether appropriate use to be made of an automated device for gel electrophoresis with automatic DNA sequencing described in U.S. Pat. No. 4,811,218 and corresponding, in particular, to the device marketed by Applied Biosystem, model 373A$^R$. With this device, suitable software makes it possible to digitize the area of fluorescence peaks recorded for each of the DNA fragments of various sizes, and to represent their relative quantities.

The synthesis of oligonucleotides labeled with a fluorescent label is well known to persons skilled in the art.

The apparatus is hence used only to measure the lengths and the intensity of the elongation products. Naturally, since there are four commercial fluophors of different "colors", different fluophors may be used, as is done in DNA sequence determinations, but for different reasons.

Some commercial apparatuses form an analysis of the four colors in 24 lanes simultaneously (equivalent to 96 samples). The analysis takes a few hours and the results are computerized.

In addition, the method according to the invention offers the possibility of carrying out multiparametric analyses, enabling several DNA fragments of different sizes to be assayed and quantified in the same sample under analysis, provided that the labeled DNA fragments originating from the standard DNA and the DNA to be quantified differ in size from one another, respectively, on the one hand, and yield DNA fragments ranging in sizes which are detectable in a single size determination, that is to say on a single lane of sequencing gel. For this purpose, it suffices to make a suitable choice of amplification oligonucleotide primers or labeled oligonucleotide primers, so as to generate fragments of different sizes during the elongation of step 3.

It is then possible, in a single size determination, to assay and quantify up to 50 genes in the same sample.

The subject of the present invention is also a process according to one of the preceding embodiments for multiparametric analysis, enabling several DNA fragments of interest to be assayed and quantified in the same sample under analysis, characterized in that:

- to the sample to be analyzed containing said DNA fragments of interest, an equal number of standard DNA fragments are added, the standard DNA fragments being different for each of the DNA fragments of interest, and
- the standard DNAs and the labeled oligonucleotides of step 3) are chosen in such a way as to generate fragments of different sizes during step 3).

In another embodiment, the subject of the present invention is a process, characterized in that, in step 3), two oligonucleotide primers different from the amplification primers of step 2), specific for the DNA fragment of interest and the standard fragment, respectively, and labeled with different labels, are added to reaction medium obtained in step 2); one or more additional amplification cycle(s) is/are then performed with said two labeled oligonucleotide primers, so that, during a cycle, after denaturation of the DNA and elongation with a DNA polymerase, said two labeled oligonucleotides generate two types of DNA fragments, labeled with different labels according to whether they originate from DNA of interest or standard DNA.

In this case, in step 4), physical separation of the standard DNA and the DNA to be quantified is optional if the intensity of the signal corresponding to each of the labels is detected directly.

In effect, the measurement of the ratio of the quantities of standard DNA and DNA of interest may be calculated if the specific activity of each of the labels is known.

As has been stated, according to the invention, the measurement of the ratio of the quantities of standard DNA and DNA to be quantified does not inevitably necessitate their physical separation, in particular by electrophoresis.

In particular, in this latter embodiment:
a) in step 2), the amplification primers may be chemically modified so that they can be linked to a solid phase, and
b) after step 3), the amplification products are linked to the solid phase via said modified primers, and the solid phase is then washed so as to remove the excess unreacted labeled primers of step 3).

Naturally, in this latter embodiment, if the labeled DNA fragment of interest and the labeled standard fragment differ in only one site, both oligonucleotide primers of step 3) include this site.

In an embodiment, the amplification primers of step 2) are biotinylated, and can react and can bind to streptavidin, which is coupled to the solid phase.

According to a variant of embodiment, the solid phase can consist of magnetic beads. A magnetic field permits a rapid sedimentation of the amplified products during the step of washing of the solid phase.

To provide for good detection of the signal, it is preferable that, if $X_o$ represents the initial quantity of the standard DNA fragment and $Y_o$ that of the DNA fragments of interest, it corresponds to the formula $$10 \cdot X_o > Y_o > \frac{1}{10} \cdot X_o.$$

For this reason, preferably, the process according to the invention is repeated several times in different tubes, under the same conditions, except for the initial quantities of standard DNA fragments, which vary according to the tube.

The process according to the invention is applicable to any process involving the use of DNA amplification methods, in particular diagnostic processes.

Lastly, the subject of the present invention is a kit for determining the quantity of a DNA fragment of interest by a process according to the invention, characterized in that it contains:

- a standard DNA fragment differing in size and/or in sequence by not more than approximately 10%, and preferably by not more than 5 nucleotides per strand, from the DNA fragment of interest;
- reactants for carrying out said method of enzymatic amplification in vitro, and in particular oligonucleotide primers;
- one or more labeled oligonucleotide primer(s), which hybridize(s) with the standard DNA fragment and the fragment of interest at a suitable site in order that an elongation with the DNA polymerase generates labeled DNA fragments of different sizes and/or sequences or with different labels according to whether they originate from the DNA fragment of interest or the standard fragment, respectively.

Other advantages and features of the present invention will become apparent in the light of the description which follows.

EXAMPLE 1

In this example, the concentration of the messenger RNAs resulting from the transcription of class I genes of the major histocompatibility complex of the mouse is measured in different organs and under different experimental conditions. For this purpose, a standard DNA is constructed from the sequence of the H-$2K^d$ gene (FIG. 1). This standard DNA is then used in the subsequent amplification experiments as a standard sample.

Materials and Methods:

1. Mice, bacterial strain and vectors.

BALB/c mice are supplied by the animal house of the Pasteur Institute.

The DNAs of interest are inserted into plasmid Bluescript pBS SK⁺. The recombinant plasmids obtained are cloned by electroporation of *E. coli* strain DH5alpha (Woodcock et al., 1989) according to the protocol described by Dower et al. (1988). Plasmid pH-$2^d$-33 was constructed by Lalanne et al. (1983).

2. Synthetic oligonucleotide primers.

The synthetic oligonucleotides were synthesized using an Applied Biosystem 381A synthesizer and the corresponding reactants. The fluorescent primer was labeled using Applied Biosystem's procedures and reactants (synthesis with aminolink at the 5' end of the oligonucleotide, followed by the actual labeling step). Only the fluophor Fam was used. The list of oligonucleotides is given below.

oligonucleotide primer H2-I (SEQ ID NO: 1): 5'-CTGACCTGGCAGTTGAATGG-3' oligonucleotide primer H2-II (SEQ ID NO: 26):
5'-TGACTATTGCAGCTCCAAGG-3'
labeled oligonucleotide primer H2-III (SEQ ID NO: 2):
5'-XCTGTGGTGGTGCCTCTTGG-3'
where X denotes the fluorescent label.

3. RNA extraction.

The RNAs were prepared using the protocol described by Chrigwin [sic] et al. (1979): the tissue of interest is ground in 7 ml of a 4M solution of guanidine isothiocyanate containing 0.5% of Na N-laurylsarcosine, 2 mM EDTA, 0.13% of antifoam A, and placed on a discontinuous cesium chloride gradient composed of 3 ml of a 5.7M solution of CsCl, 25 mM Na acetate pH 5.2, 10 mM EDTA, covered with 0.7 ml of a 2.4M CsCl, 25 mM Na acetate pH 5.2, 10 mM EDTA solution. The whole is then ultracentrifuged for 24 hours at 30,000 rpm at 20° C. in an SW41 rotor. After decantation, the pellet is resuspended in 400 µl of a 10 mM Tris-HCl pH 7.5, 1 mM EDTA, 5% Na N-laurylsarcosine, 0.1M NaCl, 5% phenol solution. The RNA is then extracted by adding one volume of phenol and one volume of chloroform. The aqueous phase is finally precipitated with ethanol and the pellet is dissolved in water.

4. Reverse transcription.

The synthesis of complementary DNA is carried out according to the protocol and using the reactants supplied in the Boehringer reverse transcription kit. In particular, the oligonucleotide used as a primer for the transcription is a poly(dT) 15-mer. 10 µg of total RNA are used in each reverse transcription experiment.

5. Amplification by the PCR method.

The amplifications are carried out in 50 µl of a solution containing 20 u/ml of the enzyme Taq polymerase (PromegaR), 200 µM each of the nucleotide triphosphates dATP, dGTP, dCTP and dTTP and 0.5 µM each of the oligonucleotides H2-I and H2-II, in the Promega buffer, the whole covered with 50 µl of mineral oil. Perkin-Elmer$^R$ and Lepscientific$^R$ Prem automated equipment was used. The amplification conditions are as follows: the sample is first heated for 1 min to 94° C. and then subjected to a number of cycles of the following programme: 1 min at 94° C., 1 min at 60° C. and 4 min at 72° C. Finally, the sample is brought to 72° C. for 10 min. The concentration of $Mg^{2+}$ ion used is 1.5 mM.

6. Additional elongation.

A 2 µl aliquot of the above PCR reaction medium is used in a "run-off" experiment. This reaction is carried out in a volume of 10 µl of a solution containing 0.1 µM fluorescent labeled primer H2-III, 20 u/ml of the enzyme Taq polymerase (Promega$^R$), 200 pM each of the nucleotide triphosphates dATP, dGTP, dCTP and dTTP, in the PromegaR buffer, the whole covered with 20 µl of mineral oil. The concentration of $Mg^{2+}$ ion used is 1.5 mM. The elongation programme is as follows: after a step of denaturation for 2 min at 94° C., the sample is brought to 60° C. for 1 minute and then 72° C. for 15 min. This reaction is carried out using the same automated equipment as for the PCR reactions.

7. Electrophoresis.

The fluorescent products of the elongation step are separated according to their size in a DNA sequencer gel using an Applied Biosystems 373A$^R$ device. The gel is 400 µm in thickness and has a concentration of 4% of acrylamide and 8M urea. The samples are mixed with 1 volume of a 99% formaldehyde, 20 mM EDTA solution, and denatured for 10 min at 80° C. 2 µl of this solution are then loaded onto the gel. Electrophoresis is carried out at 30 W for 3 hours.

8. Analysis of the electrophoresis data.

Suitable software is employed to analyze the data recorded by the Applied Biosystems 373A device. The essential features of this software are that it enables the areas of the corresponding peaks to be measured with a relative accuracy of better than 5%, and the sizes of single-stranded DNA molecule to be determined to within ±0.2 nucleotide relative to standards of ad hoc size.

Results

1. Construction of the standard DNA.

2 plasmids were constructed from pH-$2^d$-33. The KpnI-DraI fragment of plasmid pH-$2^d$-33 was introduced into the vector Bluescript pBS SK$^+$ at the KpnI and EcoRV sites. pH2, the recombinant plasmid thereby obtained, contains the 3' portion of the complementary DNA coding for the H-$2K^d$ histocompatibility antigen. From this plasmid, plasmid pH2-stand is constructed by digesting pH2 at the HindIII site and making the ends of the linearized plasmid blunt with phage T4 polymerase. When religated and cloned, this plasmid hence differs from pH2 by the addition of 4 base pairs at the HindIII site (see FIG. 1).

Finally, three oligonucleotides which hybridize in highly conserved regions of the class I H-2 genes were synthesized.

2. Determination of the saturation threshold.

In a first series of experiments, the number of amplification cycles beyond which the quantity of DNA ceases to grow exponentially as a function of the number of amplification cycles was determined for a certain initial quantity of DNA.

Variable quantities of plasmid pH2-stand were hence amplified in parallel experiments. The quantities of DNA vary from $10^2$ to $10^8$ copies of plasmid, and the number of amplification cycles from 20 to 45 cycles.

It was shown that the threshold beyond which amplification ceases to be exponential is variable, even if the initial concentration of DNA is the same. However, under the experimental conditions described, when more than 1,000 copies of plasmid pH-stand are amplified, this threshold is reached in all cases before 30 amplification cycles. In all the experiments reported below, all the amplifications are carried out "at saturation", since more than 1,000 copies of the standard DNA are amplified during 40 cycles.

3. Quantification of an H-$2K^d$ plasmid with the standard DNA.

It was next shown that the protocol described does indeed make it possible to determine the concentration of plasmid pH2, knowing the concentration of the standard DNA pH2-stand.

For this purpose, approximately 7,000 copies of plasmid pH2 (obtained after dilution of a solution whose concentration is determined by measuring the optical density at 260 nm) were mixed with 1,000, 10,000 and 100,000 copies of plasmid pH2-stand. These different mixtures were amplified, and the results are recorded in FIG. 2; FIG. 2a) shows that the resolution of the electrophoretic separation is sufficient to separate the elongation products emanating from the two amplified species. For the same sample amplified in different experiments, the areas of each of the peaks vary from one experiment to another, whereas the ratios between these areas are remarkably reproducible. FIG. 2b) shows that it is then easy to determine the initial concentration of plasmid pH2. Similar experiments were carried out, varying the number of copies of plasmid pH2 from 100 to 1,000,000 copies. Identical results were obtained, except when the number of copies is too low: in this case, quantification is less reliable.

4. Quantification of the concentration of the MHC class I gene transcripts in different organs.

This method was then applied to the determination of the number of copies of complementary DNA present after the reverse transcription of a known quantity of total RNA of a number of tissues. For this purpose, the RNA of various tissues of BALB/c mice (H2$^k$ haplotype) was prepared. 10 μg of total RNA were used for the synthesis of complementary DNA. 1/50 of these complementary DNAs was then mixed with variable quantities of plasmid pH2-stand. The results of the quantification from the RNA of a few organs are shown in FIG. 3. In this experiment, the complementary DNA synthesized is a single-stranded DNA, whereas the standard DNA is a double-stranded DNA. To take account of this difference, the concentrations obtained were multiplied by two.

The number of copies of complementary DNA present after the reverse transcription of 100 ng of total RNA are hence:

in the lung: $50 \times 10^5$ copies, in the thymus: $8 \times 10^5$ copies in the brain: $2 \times 10^5$ copies.

5. Measurement of the increase in concentration of the MHC class I gene transcripts in the liver after induction of an acute phase.

Figure 4:
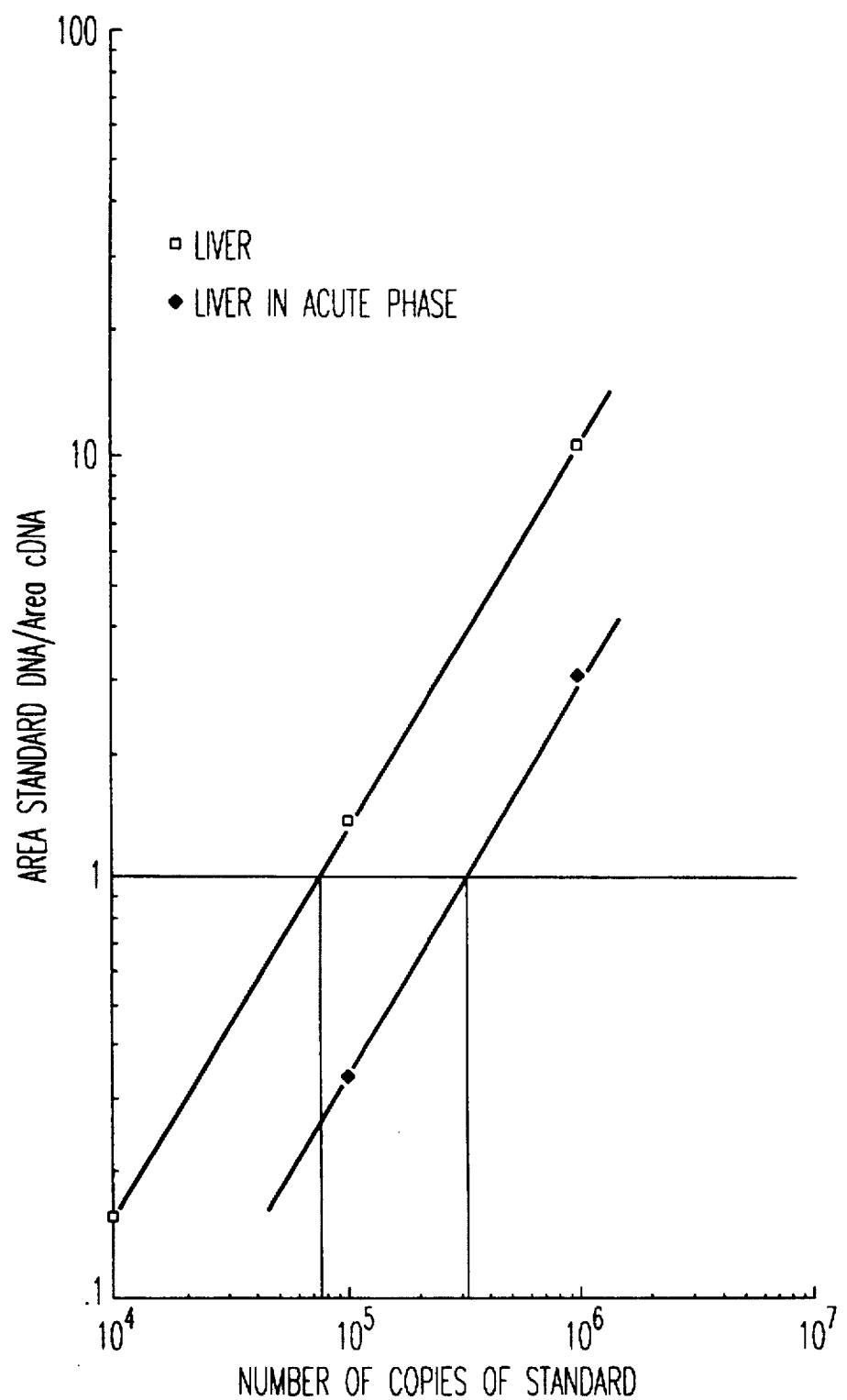
Figures 8A, 8B, 8C, 8D:

Finally, the concentration of complementary DNAs of the transcripts of the class I H-2 genes in a BALB/c mouse liver in acute phase 24 hours after the injection of LPS was compared with the concentration of these complementary DNAs in the liver of a control mouse. The results of the quantification of these complementary DNAs are shown in FIG. 4. A change by a factor of 3 is readily detected.

EXAMPLE 2

RNA was extracted from a T cell tumor (BW 5147, Barth et al., 1985), the T cell receptor of which was characterized by sequencing the mRNAs coding for the alpha and beta chains. A single-stranded cDNA was synthesized and used as a DNA fragment of interest in subsequent amplifications. It was desired to quantify the number of transcripts coding for the beta chain of this receptor per cell.

In this case, instead of using a cDNA having a mutated sequence as an internal standard sample, a cDNA already cloned into plasmid K17, which gives elongation products smaller by 5 nucleotides than the cDNA to be quantified (BW 5147 sequence) and which differs therefrom in size by 5 nucleotides and in sequence by 11 nucleotides, was used. The sequence of the DNA fragment to be quantified (BW 5147) comprised more than 170 nucleotides. The comparative sequences of BW 5147 and K17 are given in FIG. 5.

Various quantities of standard (K17) were added, mixed and coamplified to saturation with the cDNA to be quantified, saturation being obtained after 40 cycles using the V and C primers.

An aliquot of this amplification medium was used as a template in the elongation reaction with the third primer J common to the standard DNA fragment and the fragment of interest.

The labeled DNA fragments originating from the standard DNA fragment and the fragment of interest (cDNA) were separated physically by gel electrophoresis, and the ratio of the quantities of the standard DNA fragment and the fragment of interest was measured by measuring the intensity of the signal (area of the fluorescence peaks) corresponding to the two types of fragments.

Materials and Methods

1. Bacterial strain and vectors

The DNAs of interest consist of cDNAs corresponding to transcripts of genes coding for the beta chain of mouse T cell receptors.

Plasmid K17 contains the standard DNA fragment, and was constructed from the vector M13m p18 (Biolabo) which was rendered in the form of single-stranded DNA in the capsid of the bacteriophage m13.

2. Synthetic oligonucleotides

The oligonucleotide primers were synthesized using an Applied Biosystem 381A synthesizer and the corresponding reactants. The fluorescent primers were labeled using Applied Biosystem's procedures and reactants. The fluophor Fam was used for the most part, but three others were also used with similar results. The list of oligonucleotides is given below.

V (SEQ ID NO: 6): CTGAATGCCCAGACAGCTC-CAAGC

C (SEQ ID NO: 27): CTTGGGTGGAGTCACATTTCTC

J (SEQ ID NO: 28): XGTGCCTGGCCCAAAGTACTGG where X is the fluorescent label.

3. PCR method

The amplifications were carried out using Perkin Elmer Cetus and Prem automated equipment, according to the technique described (Saiki et al., 1988).

To amplify the complementary DNA, the protocol used was as follows: 5 μl of the previously prepared solution are amplified in 50 or 100 μl of a solution comprising 50 mM KCl, 10 mM Tris-HCl pH 8.2, 0.01% gelatin, 0.5 μM each of the two oligonucleotides V and C, 2 μ per 100 μl of Taq polymerase (Beckman) and 200 μM each of the nucleotides dATP, dGTP, dCTP and dTTP. The whole is covered with 50 μl of mineral oil, heated for 1 min to 94° C., amplified by 40 cycles (1 min at 94° C., 1 min at 60° C., 1 min at 72° C., and then incubated for 10 min at 72° C.

4. Additional elongation

A 2 μl aliquot of the above PCR reaction medium was used in a "run-off" experiment; the fluorescent labeled primer (Jbeta 2.5) was added to a final concentration of 0.1 μM in the same mixture as that used for the amplification.

The J primer is hence in excess relative to the other primers V and C introduced with the μl [sic] of the amplified mixture. The "run-off" reaction consists of 2 min at 94° C., 1 min at 60° C. followed by 15 min at 72° C.

5. Separation of the amplified products according to their size

The amplified products labeled with the fluorescent label were separated according to their size in a sequencer gel using an Applied Biosystems 373A device with automated DNA sequencer. Suitable software was used, enabling the fluorescence peaks recorded to be digitized.

6. Electrophoresis

Analysis of the amplification products and the sequences is carried out by electrophoresis on 6% polyacrylamide gel (crosslinking: 1 g of bisacrylamide per 19 g of acrylamide) 400 μm in thickness, in TBE buffer (Maniatis et al., 1982) under denaturing conditions (95% formamide, 20 mM EDTA, and incubated for 10 min at 80° C. Migration is carried out in TBE buffer under an electric field of 4,000 Vm$^{-1}$ for 5 to 6 h for the analysis of products of the "run-off" step.

EXAMPLE 3

A 1 milliliter blood sample was drawn from a BALB/c mouse. In this blood sample, a large number of T lymphocytes, which express at their surface receptors (TCR) involved in the recognition of antigens by these cells, are present. The two genes coding for the alpha and beta chains of this receptor are formed from gene segments (referred to as V, D, J and C) rearranged during one of the steps of maturation of the cell. The rearrangements take place in such a way that the junctions between the V and J segments have sequences whose length can vary by a few nucleotides. This length (variable from cell to cell) is referred to as "length of the CDR3 region". It was desired to quantify the number of transcripts coding for the beta chain of this receptor per μg of RNA extracted, when the gene coding for this beta chain utilizes certain V and J segments taken from the segments available in the genome of the mouse. More specifically, the number of transcripts coding for beta chains utilizing the Vbeta6 and Jbeta1.5 gene segments and having a certain length of the CDR3 region is determined here. A double-stranded cDNA was synthesized and used in the subsequent amplifications.

A cDNA coding for one of these chains, and cloned into a plasmid, is used as an internal standard sample. This chain has a length of the CDR3 region equal to 7 amino acids.

Variable quantities of this plasmid were added, mixed and coamplified to saturation with the cDNA to be quantified, saturation being obtained after 40 cycles using the V and C primers.

An aliquot of this amplification medium was used as a template in the elongation reaction with the third primer J common to the [lacuna] DNA fragment and the fragment of interest.

Physical separation is performed by gel electrophoresis according to the same protocol as in Example 1.

Materials and Methods

1. The cDNA constituting the standard is cloned into the vector Bluescript pBS SK$^+$, using an *E. coli* strain XL1 Blue as host.
2. The list of oligonucleotides used is given below.
V (SEQ ID NO: 29): CTCTCACTGTGACATCTGCCC
J (SEQ ID NO: 30): XGAGTCCCCTCTCCAAAAAGCG
C (SEQ ID NO: 27): CTTGGGTGGAGTCACATTTCTC
where X is the fluorescent label.
3. The remaining methods are identical to those employed in Example 1.

Results

FIG. 6 shows that:

in the population of T lymphocytes drawn with the blood sample, there are some which have T receptors in which the beta chain utilizes the Vbeta6 and Jbeta1.5 segments and in which the length of the CDR3 region varies from 7 to 10 amino acids.

moreover, when fewer than 300 copies of the plasmid containing the standard DNA are added before amplification, the quantity of amplified DNA having a length of the CDR3 equal to 7 amino acids remains unchanged, to within the accuracy of the measurements, relative to the quantity of DNA having a length of the cDR3 region other than 7. In contrast, when 3,000 or more copies of the standard DNA are added, a contribution due to the standard DNA is observed in the signal generated by the cDNAs having a length of the CDR3 equal to 7. This relative contribution to the signal is calculated by subtracting from the total signal the signal obtained when no standard DNA is added. The table shows that this contribution varies in the same ratio as the number of copies of the standard DNA added (like [sic] 1 and 3 of the table).

During each of these amplifications, the cDNA obtained from the reverse transcription of 100 ng of extracted RNA is used. It is hence estimated that the number of transcripts present in these 100 ng of total RNA, coding for beta chains utilizing the Vbeta- [sic] and Jbeta1.5 segments and having, in addition, a length of the CDR3 equal to 7, is 3,000×560/140, or 12,000 copies. The quantity of these transcripts in which the length of the CDR3 is equal to 8, 9 or 10 amino acids may likewise be deduced.

TABLE 2

| Number of copies of the plasmid | Intensity of the peak of 7 aa | Signal generated by the plasmid |
|---|---|---|
| 0 | 560 | 0 |
| 300 | 530 | 0 |
| 3,000 | 700 | 140 |
| 30,000 | 1,970 | 1,410 |
| 300,000 | 12,940 | 12,380 |

EXAMPLE 4

Another practical advantage of the process according to the invention is that it makes it possible, for different samples for which there is suitable spacing between the primers and reference standards, to perform analysis on the same gel. It has thus been possible to develop a test which permits simultaneous measurements of mRNA coding for a variety of oncogenes for the characterization of human or murine tumors.

In this example, the concentration is measured of the messenger RNAs resulting from the transcription of different murine genes in the biopsies of tumors derived from mastocytoma P815, in DBA/2 mice (Van den Eynde et al., 1991).

For this purpose, the complementary DNAs are synthesized by reverse transcription of a specified quantity (10 μg) of total RNA prepared from the biopsy. In this population of complementary DNAs, the number of copies of cDNA coding for different genes of interest is quantified according to the method described in the present invention.

The transcripts of interest are: aldolase H (Mestek et al., 1987; Maire et al., 1987) and ubiquitin, the genes for which are expressed ubiquitously, the messenger RNAs of the PIA gene coding for one of the antigenic determinants of tumor p815 (Van den Eynde et al., 1991), and the messenger RNAs of the class I genes of the major histocompatibility complex already described in Example 1. For each of these 6 genes (or families of genes), a plasmid DNA is synthesized as described in Examples 1 and 2. These 4 standard DNAs are used in the subsequent amplifications to determine the number of copies of complementary DNA for each of these 4 (families of) genes, as described in Example 1.

The oligonucleotides are synthesized in such a way that the fluorescent extension products emanating from these 4 quantifications, when mixed, may be analyzed simultaneously on the same lane of the electrophoresis gel.

The sequences of the oligonucleotides used are given below, together with the sizes in nucleotides of the amplification products and products of the additional elongation. The nomenclature used for designation of the primers is the same as that employed in Example 1: for each gene, the primers I and II are used in the amplification, while the primer III is fluorescent and used in the additional elongation.

List of oligonucleotides used:

| Sequence 5' to 3' | | Size of the amplification product | Size of the elongation product |
|---|---|---|---|
| aldolase H gene: | | 290 | 108 |
| Ald - I (SEQ ID NO: 11): | GACCCACCCCGTCCTGTGCC | | |
| Ald - II (SEQ ID NO: 31): | CTCGTGGAAGAGGATCACCC | | |
| Ald - III (SEQ ID NO: 32): | XGGTGAGCGATGTCAGACAGCTCC | | |
| ubiquitin gene: | | 247 | 122 |
| Ubi - I (SEQ ID NO: 16): | GACGGGCAAGACCATCACTC | | |
| Ubi - II (SEQ ID NO: 33): | AGTTGTACTTCTGGGCAAGC | | |
| Ubi - III (SEQ ID NO: 34): | XGGAGGATGGCCGCACCCTGTCC | | |
| P1A gene: | | 442 | 146 |
| P1A - I (SEQ ID NO: 21): | AACAAGAAACCAGACAAAGCC | | |
| P1A - II (SEQ ID NO: 35): | CACAGTTAGCGCCAGCACC | | |
| P1A - III (SEQ ID NO: 36): | XGCCAGAAAACTTGTTGTGACAACAGC | | |
| class I H2 gene: | | 253 | 159 |
| H2 - I (SEQ ID NO: 1): | CTGACCTGGCAGTTGAATGG | | |
| H2 - II (SEQ ID NO: 26): | TGACTATTGCAGCTCCAAGG | | |
| H2 - III (SEQ ID NO: 2): | XCTGTGGTGGTGCCTCTTGG | | |

The process according to the present invention has proved amazingly reliable, accurate and reproducible during a large number of experiments. The possibility of performing the measurement at saturation simplifies the simultaneous analyses of multiple samples and increases the sensitivity of detection at the end of the reaction.

REFERENCES

Barth, R. K., Kim, B. S., Lan, N.C., Hunkapiller, T., Sobieck, N. Winoto, A., Gershenfeld, H., Okada, C., Ilansburg, D., Weissman, I. L., and Hood, L. (1985). The murine T-cell receptor uses a limited repertoire of expressed Vbeta gene segments. Nature 316, 517–523.

Chirgwin, J. M., Przybyla, A. E., MacDonald, R. J., and Rutter, W. J. (1979). Isolation of biologically active ribonucleic acid from sources enriched in ribonuclease—Biochemistry 18, 5294–5299.

Dower, W. J., Miller, J. F., and Ragsdale, C. (1988). High efficiency transformation of E. Coli by high voltage electroporation. Nucl. Acids. Res. 16, 6127–6145.

Erlich, H. A., Gelfand, D., and Sninsky, J. J. (1991). Recent advances in the polymerase chain reaction. Science 252, 1643–1650.

Gilliland, G., Perrin, S., Blanchard, K., and Bunn, H. F. (1990). Analysis of cytokine mRNA and DNA: Detection and quantitation by competitive polymerase chain reaction. Proc. Natl. Acad. Sci. 87, 2725–2729.

Kellog, D. E., Sninsky, J. J., and Kwok S. (1990). Quantitation of HIV-1 proviral DNA relative to cellular DNA by the polymerase chain reaction. Anal. Biochem 189, 202–208.

Mullis, K. B. and Faloona, F. (1987). Specific synthesis of DNA in vitro via a polymerase-catalyzed chain reaction. Methods Enzymol. 155 335–350.

Lalanne, J.-L., Delarbre, C., Gachelin, G., and Kourilsky, P. (1983). A cDNA clone containing the entire coding sequence of a mouse H-2Kd histocompatibility antigen. Nucl. Acids Res. 11, 1567–1577.

Maire, P., Gautron, S., Hakim, V., Gregori, C., Mennecier, F., and Kahn, A. (1987). Characterization of three optional promoters in the 5' region of the human aldolase A gene. J. Mol. Biol. 197, 425–438.

Mestek, A., Stauffer, J., Tolan, D. R., and Ciejek-Baez, E. (1987). Sequence of a mouse brain aldolase A cDNA. Nucl. Acids Res. 15, 10595.

Robinson, M. O., and Simon, M. I. (1991). Determining transcript number using the polymerase chain reaction: Pgkk-2, mP2, and POK-2 transgene mRNA levels during spermatogenesis. Nucleic Acids Res. 19, 1557–1562.

Saiki, R. K., Scharf, S., Faloona, F., Mullis, K. B., Horn, G. T. Erlich, II. A., Arnheim, N. (1985). Enzymatic amplification of beta-globin genomic sequences and restriction site analysis for diagnostic [sic] of sickle cell anemia, Science 230, 1350–1354.

Singer-Sam, J., Robinson, M. O., Bellivé, A. R., Simon, M. I., and Riggs, A. D. (1990). Measurement by quantitative PCR of changes in MPRT, PGK-1, PGK-2, APRT, MTase, and Zfy gene transcripts during mouse spermatogenesis. Nucleic Acids Res. 18, 1255–1259.

Van den Eynde, B., Lethé, B., Van Pel, A., De Plaen, E., and Boon, T. (1991). The gene coding for a major tumor rejection antigen of tumor P815 is identical to the normal gene of syngeneic DBA/2 mice. J. Exp. Med. 173, 1373–1384.

Wang, A. M. Doyle, M. V., and Mark, D. F. (1989). Quantitation of mRNA by the polymerase chain reaction. Proc. Natl. Acad. Sci. 86, 9711–9721.

Woodcock, D. M., Crawther, P. J., Doherty, J., Jefferson, S., Debruz, E., Noyer-Weidner, M. Smith, S. S., Michael, M. Z., and Graham M. W. (1989)—Quantitative evolution of Escherichia Coli host strains for tolerance to cytosine methylation in plasmid and phage recombinants. Nucl. Acids Res. 17, 3469–3478.

We claim:

1. A process for determining in vitro the quantity of a DNA fragment of interest in a sample, comprising the steps of:
   adding a standard DNA fragment to said sample, each of said standard DNA fragment and said DNA fragment of interest having 5' and 3' ends, said 5' and 3' ends of said standard DNA fragment being identical to said 5' and 3' ends of said DNA fragment of interest, respectively; thus permitting amplification with a set of two primers, said standard DNA fragment and said DNA fragment of interest having a site which differs in sequence, in size, or in both sequence and in size, by at least one nucleotide but not more than approximately 10%,
   co-amplifing said standard DNA fragment and said DNA fragment of interest with said set of primers to saturation,
   elongating said saturated standard DNA fragment and said saturated DNA fragment of interest in the presence of a DNA polymerase using a first labeled primer and a second labeled primer, where said first labeled primer hybridizes specifically to said standard DNA fragment downstream from said 5' end of said standard DNA fragment and upstream of said site which differs in sequence, in size, or in both sequence and in size, and said second labeled primer hybridizes specifically to said DNA fragment of interest downstream from said 5' end of said DNA fragment of interest and upstream of said site which differs in sequence, in size, or in both sequence and in size, to obtain a labeled standard DNA fragment having a first label and labeled DNA fragment of interest having a second label, and
   determining the ratio of said standard DNA fragment to said DNA fragment of interest.

2. The process of claim 1, wherein each of said identical ends is a sequence of from 15 to 25 nucleotides.

3. The process of claim 2, wherein said standard DNA fragment consists of from 50 to 500 nucleotides, and said standard DNA fragment differs from said DNA fragment of interest in sequence, in size, or in both sequence and in size, by from two to five nucleotides.

4. The process of claim 3, wherein said standard DNA fragment differs from said DNA fragment of interest by a deletion, mutation or addition of three or four nucleotides.

5. The process of claim 1, wherein said site which differs in sequence, in size, or in both sequence and in size is a restriction site, and said process further comprises the step of digesting said standard DNA fragment with the corresponding restriction enzyme after said elongating step and before said determining step.

6. The process of claim 1, wherein said determining step comprises separating said labelled standard DNA fragment and said labelled DNA fragment of interest by gel electrophoresis.

7. The process of claim 6, wherein said separating step comprises gel electrophoresis with DNA sequencing.

8. The process of claim 1, wherein said label is a radioactive, enzymatic, or fluorescent label.

9. The process of claim 8, wherein said label is an enzymatic or fluorescent label.

10. The process of claim 1, wherein said process determines in vitro the quantity of up to 50 DNA fragments of interest in a sample and a number of standard DNA fragments are added equal to the number of DNA fragments of interest, said standard DNA fragments and said DNA fragments of interest being chosen in a manner which generates fragments of different sizes after said elongating step.

11. The process of claim 10, wherein said first primer and said second primer contain a means for linking said first primer and said second primer to a solid phase, and said process further comprises the step of linking said labeled standard DNA fragment and said labeled DNA fragment of interest to said solid phase after said elongating step and prior to said determining step, and washing said solid phase prior to said determining step.

12. The process of claim 1, wherein said DNA fragment of interest and said standard DNA fragment differ in only one site, said elongating step is conducted in the presence of a first labeled primer which hybridizes to said standard DNA fragment and a second labeled primer which hybridizes to said DNA fragment of interest at a location including said site.

13. The process of claim 11, wherein said first primer and said second primer are biotinylated, and said solid phase is coupled to streptavidin.

14. The process of claim 1, wherein said process is repeated using a quantity of said standard DNA fragment which differs from said first quantity of said standard DNA fragment.

15. The process of claim 1, wherein said label is a fluorescent label.

16. The process of claim 1, wherein said co-amplifying step comprises a polymerase chain reaction.

17. The method of claim 1, wherein said standard DNA fragment and said DNA fragment of interest differ in size.

18. A process for determining in vitro the ratio of a DNA fragment of interest in a sample to a standard DNA fragment, consisting essentially of the steps of:
   adding a standard DNA fragment to said sample, each of said standard DNA fragment and said DNA fragment of interest having 5' and 3' ends, said 5' and 3' ends of said standard DNA fragment being identical to said 5' and 3' ends of said DNA fragment of interest, respectively, thus permitting amplification of both of said standard DNA fragment and said DNA fragment of interest with a set of two primers, said standard DNA fragment and said DNA fragment of interest having a site which differs in sequence, in size, or in both sequence and in size, by at least one nucleotide but not more than approximately 10%,
   co-amplifying said standard DNA fragment and said DNA fragment of interest with said set of primers to saturation,
   elongating said saturated standard DNA fragment and said saturated DNA fragment of interest in the presence of a DNA polymerase using one labeled primer which hybridizes specifically to said standard DNA fragment downstream from said 5' end of said standard DNA fragment and said DNA fragment of interest, and upstream of said site which differs in sequence, in size, or in both sequence and in size to obtain a labeled standard DNA fragment and labeled DNA fragment of interest, and determining the ratio of said standard DNA fragment to said DNA fragment of interest.

19. The process of claim 18, wherein said site which differs in sequence, in size, or in both sequence and in size is a restriction site, and said process further consists essentially of the step of digesting said standard DNA fragment with the corresponding restriction enzyme after said elongating step and before said determining step.

20. The process of claim 18, wherein each of said 5' and 3' ends is a sequence of from 15 to 25 nucleotides.

21. The method of claim 18, wherein said DNA fragment of interest and said standard DNA fragment differ in size.

22. The method of claim 18, wherein said elongating step consists of hybridizing said labeled primer to standard DNA fragment and said DNA fragment of interest, and performing an elongation in the presence of said DNA polymerase and unlabelled.

23. The process of claim 18, wherein said standard DNA fragment consists of from 50 to 500 nucleotides, and said standard DNA fragment differs from said DNA fragment of interest in sequence, in size, or in both sequence and in size, by from two to five nucleotides.

24. The process of claim 18, wherein said label is an enzymatic or fluorescent label.

25. The process of claim 18, wherein said standard DNA fragment differs from said DNA fragment of interest by a deletion, mutation or addition of three or four nucleotides.

26. The process of claim 18, wherein said process determines in vitro the quantity of up to 50 DNA fragments of interest in a sample and a number of standard DNA fragments are added equal to the number of DNA fragments of interest, said standard DNA fragments and said DNA fragments of interest being chosen in a manner which generates fragments of different sizes after said elongating step.

27. The process of claim 26, wherein said first primer and said second primer contain a means for linking said first primer and said second primer to a solid phase, and said process further comprises the step of linking said labeled standard DNA fragment and said labeled DNA fragment of interest to said solid phase after said elongating step and prior to said determining step, and washing said solid phase prior to said determining step.

* * * * *

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

| | |
|---|---:|
| CTGACCTGGC AGTTGAATGG | 20 |

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

| | |
|---|---:|
| NCTGTGGTGG TGCCTCTTGG | 20 |

( 2 ) INFORMATION FOR SEQ ID NO:3:

( i ) SEQUENCE CHARACTERISTICS:
        ( A ) LENGTH: 293 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

| | | | | | | |
|---|---|---|---|---|---|---:|
| GCCCTGGGCT | TCTACCCTGC | TGATATCACC | CTGACCTGGC | AGTTGAATGG | GGAGGACCTG | 60 |
| ACCCAGGACA | TGGAGCTTGT | AGAGACCAGG | CCTGCAGGGG | ATGGAACCTT | CCAGAAGTGG | 120 |
| GCAGCTGTGG | TGGTGCCTCT | TGGGAAGGAG | CAGAATTACA | CATGCCATGT | GCACCATAAG | 180 |
| GGGCTGCCTG | AGCCTCTCAC | CCTGAGATGG | AAGCTTCCTC | CATCCACTGT | CTCCAACACG | 240 |
| GTAATCATTG | CTGTTCTGGT | TGTCCTTGGA | GCTGCAATAG | TCACTGGAGC | TGT | 293 |

( 2 ) INFORMATION FOR SEQ ID NO:4:

( i ) SEQUENCE CHARACTERISTICS:
        ( A ) LENGTH: 297 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

| | | | | | | |
|---|---|---|---|---|---|---:|
| GCCCTGGGCT | TCTACCCTGC | TGATATCACC | CTGACCTGGC | AGTTGAATGG | GGAGGACCTG | 60 |
| ACCCAGGACA | TGGAGCTTGT | AGAGACCAGG | CCTGCAGGGG | ATGGAACCTT | CCAGAAGTGG | 120 |
| GCAGCTGTGG | TGGTGCCTCT | TGGGAAGGAG | CAGAATTACA | CATGCCATGT | GCACCATAAG | 180 |
| GGGCTGCCTG | AGCCTCTCAC | CCTGAGATGG | AAGCTAGCTT | CCTCCATCCA | CTGTCTCCAA | 240 |

```
CACGGTAATC  ATTGCTGTTC  TGGTTGTCCT  TGGAGCTGCA  ATAGTCACTG  GAGCTGT        297
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:5:

```
GGAACCTCGA  CGTTATCAGT                                                      20
```

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:6:

```
CTGAATGCCC  AGACAGCTCC  AAGC                                                24
```

( 2 ) INFORMATION FOR SEQ ID NO:7:

( i ) SEQUENCE CHARACTERISTICS:
        ( A ) LENGTH: 189 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:7:

```
AGTCGTTTTA  TACCTGAATG  CCCAGACAGC  TCCAAGCTAC  TTTTACATAT  ATCTGCCGTG       60
GATCCAGAAG  ACTCAGCTGT  CTATTTTGT   GCCAGCAGCC  AGATAACTAG  TAACCAAGAC      120
ACCCAGTACT  TTGGGCCAGG  CACTCGGCTC  CTCGTGTAGA  GGATCTGAGA  AATGTGACTC      180
CACCCAAGG                                                                  189
```

( 2 ) INFORMATION FOR SEQ ID NO:8:

( i ) SEQUENCE CHARACTERISTICS:
        ( A ) LENGTH: 184 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

```
AGTCGTTTTA  TACCTGAATG  CCCAGACAGC  TCCAAGCTAC  TTTTACATAT  ATCTGCCGTG       60
GATCCAGAAG  ACTCAGCTGT  CTATTTTGT   GCCAGCAGCC  AACGACTGGG  GGAGACACCA     120
GTACTTTGGG  CCAGGCACTC  GGCTCCTCGT  GTAGAGGATC  TGAGAAATGT  GACTCCACCC     180
AAGG                                                                       184
```

( 2 ) INFORMATION FOR SEQ ID NO:9:

( i ) SEQUENCE CHARACTERISTICS:
        ( A ) LENGTH: 21 base pairs ( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:9:

CCAGTACTTT GGGCCAGGCA C    21

( 2 ) INFORMATION FOR SEQ ID NO:10:

( i ) SEQUENCE CHARACTERISTICS:
( A ) LENGTH: 22 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:10:

GAGAAATGTG ACTCCACCCA AG    22

( 2 ) INFORMATION FOR SEQ ID NO:11:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:11:

GACCCACCCC GTCCTGTGCC    20

( 2 ) INFORMATION FOR SEQ ID NO:12:

( i ) SEQUENCE CHARACTERISTICS:
( A ) LENGTH: 350 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:12:

AGTCCTTTCG CCTACCCACC GGCGTACCAG GCAGACCCAC CCCGTCCTGT GCCAGGAAAG    60
CAACTGCCAC CGGCACCATG CCCCACCCAT ACCCAGCACT GACCCCGGAG CAGAAGAAGG    120
AGCTGTCTGA CATCGCTCAC CGCATTGTGG CTCCGGGCAA GGGCATCCTG GCTGCAGATG    180
AGTCCACCGG AAGCATTGCC AAGCGCCTGC AGTCCATTGG CACCGAGAAC ACCGAGGAGA    240
ACAGGCGCTT CTACCGCCAG CTGCTGCTGA CTGCAGACGA CCGTGTGAAT CCCTGCATTG    300
GGGGGGTGAT CCTCTTCCAC GAGACACTGT ACCAGAAGGC AGATGATGGA    350

( 2 ) INFORMATION FOR SEQ ID NO:13:

( i ) SEQUENCE CHARACTERISTICS:
( A ) LENGTH: 346 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:13:

AGTCCTTTCG CCTACCCACC GGCGTACCAG GCAGACCCAC CCCGTCCTGT GCCAGGAAAG    60

| | | | | | |
|---|---|---|---|---|---|
| CAACTGCCAC | CGGCACCCCC | ACCCATACCC | AGCACTGACC | CCGGAGCAGA | AGAAGGAGCT | 120 |
| GTCTGACATC | GCTCACCGCA | TTGTGGCTCC | GGGCAAGGGC | ATCCTGGCTG | CAGATGAGTC | 180 |
| CACCGGAAGC | ATTGCCAAGC | GCCTGCAGTC | CATTGGCACC | GAGAACACCG | AGGAGAACAG | 240 |
| GCGCTTCTAC | CGCCAGCTGC | TGCTGACTGC | AGACGACCGT | GTGAATCCCT | GCATTGGGGG | 300 |
| GGTGATCCTC | TTCCACGAGA | CACTGTACCA | GAAGGCAGAT | GATGGA | | 346 |

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

GGAGCTGTCT GACATCGCTC ACC                                                          23

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

GGGTGATCCT CTTCCACGAG                                                            20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:16:

GACGGGCAAG ACCATCACTC                                                            20

( 2 ) INFORMATION FOR SEQ ID NO:17:

( i ) SEQUENCE CHARACTERISTICS:
        ( A ) LENGTH: 292 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:17:

| | | | | | |
|---|---|---|---|---|---|
| CGCGCCAACA | TGCAGATCTT | CGTGAAGACC | CTGACGGGCA | AGACCATCAC | TCTTGAGGTC | 60 |
| GAGCCCAGTG | ACACCATCGA | GAATGTCAAG | GCCAAGATCC | AAGACAAGGA | AGGCATCCCA | 120 |
| CCTGACCAGC | AGAGGCTGAT | ATTCGCGGGC | AAACAGCTGG | AGGATGGCCG | CACCCTGTCC | 180 |
| GACTACAACA | TCCAGAAAGA | GTCCACCTTG | CACCTGGTGC | TGCGTCTGCG | CGGTGGCATC | 240 |
| ATTGAGCCAT | CCCTTCGTCA | GCTTGCCCAG | AAGTACAACT | GTGACAAGAT | GA | 292 |

( 2 ) INFORMATION FOR SEQ ID NO:18:

( i ) SEQUENCE CHARACTERISTICS:
    ( A ) LENGTH: 288 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:18:

```
CGCGCCAACA TGCAGATCTT CGTGAAGACC CTGACGGGCA AGACCATCAC TCTTGAGGTC      60
GAGCCCAGTG ACACCATCGA GAATGTCAAG GCCAAGATCC AAGACAAGGA AGGCATCCCA     120
CCTGACCAGC AGAGGCTGAT ATTCGCGGGC AAACAGCTGG AGGATGGCCG CACCCTGTCC     180
GACTACAACA TCCAGAAAGA GTCCACCTTG CACCTGGTGC TCTGCGCGGT GGCATCATTG     240
AGCCATCCCT TCGTCAGCTT GCCCAGAAGT ACAACTGTGA CAAGATGA                  288
```

( 2 ) INFORMATION FOR SEQ ID NO:19:

( i ) SEQUENCE CHARACTERISTICS:
    ( A ) LENGTH: 22 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:19:

```
GGAGGATGGC CGCACCCTGT CC                                               22
```

( 2 ) INFORMATION FOR SEQ ID NO:20:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:20:

```
GCTTGCCCAG AAGTACAACT                                                  20
```

( 2 ) INFORMATION FOR SEQ ID NO:21:

( i ) SEQUENCE CHARACTERISTICS:
    ( A ) LENGTH: 21 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:21:

```
AACAAGAAAC CAGACAAAGC C                                                21
```

( 2 ) INFORMATION FOR SEQ ID NO:22:

( i ) SEQUENCE CHARACTERISTICS:
    ( A ) LENGTH: 500 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:22:

```
CCTTTGTGCC ATGTCTGATA ACAAGAAACC AGACAAAGCC CACAGTGGCT CAGGTGGTGA      60
```

```
CGGTGATGGG AATAGGTGCA ATTTATTGCA CCGGTACTCC CTGGAAGAAA TTCTGCCTTA    120

TCTAGGGTGG CTGGTCTTCG CTGTTGTCAC AACAAGTTTT CTGGCGCTCC AGATGTTCAT    180

AGACGCCCTT TATGAGGAGC AGTATGAAAG GGATGTGGCC TGGATAGCCA GGCAAAGCAA    240

GCGCATGTCC TCTGTCGATG AGGATGAAGA CGATGAGGAT GATGAGGATG ACTACTACGA    300

CGACGAGGAC GACGACGACG ATGCCTTCTA TGATGATGAG GATGATGAGG AAGAAGAATT    360

GGAGAACCTG ATGGATGATG AATCAGAAGA TGAGGCCGAA GAAGAGATGA GCGTGGAAAT    420

GGGTGCCGGA GCTGAGGAAA TGGGTGCTGG CGCTAACTGT GCCTGTGTTC CTGGCCATCA    480

TTTAAGGAAG AATGAAGTGA                                                500
```

( 2 ) INFORMATION FOR SEQ ID NO:23:

( i ) SEQUENCE CHARACTERISTICS:
        ( A ) LENGTH: 496 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:23:

```
CCTTTGTGCC ATGTCTGATA ACAAGAAACC AGACAAAGCC CACAGTGGCT CAGGTGGTGA     60

CGGTGATGGG AATACAATTT ATTGCACCGG TACTCCCTGG AAGAAATTCT GCCTTATCTA    120

GGGTGGCTGG TCTTCGCTGT TGTCACAACA AGTTTTCTGG CGCTCCAGAT GTTCATAGAC    180

GCCCTTTATG AGGAGCAGTA TGAAAGGGAT GTGGCCTGGA TAGCCAGGCA AAGCAAGCGC    240

ATGTCCTCTG TCGATGAGGA TGAAGACGAT GAGGATGATG AGGATGACTA CTACGACGAC    300

GAGGACGACG ACGACGATGC CTTCTATGAT GATGAGGATG ATGAGGAAGA AGAATTGGAG    360

AACCTGATGG ATGATGAATC AGAAGATGAG GCCGAAGAAG AGATGAGCGT GGAAATGGGT    420

GCCGGAGCTG AGGAAATGGG TGCTGGCGCT AACTGTGCCT GTGTTCCTGG CCATCATTTA    480

AGGAAGAATG AAGTGA                                                    496
```

( 2 ) INFORMATION FOR SEQ ID NO:24:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:24:

```
CGCTGTTGTC ACAACAAGTT TTCTGGC                                         27
```

( 2 ) INFORMATION FOR SEQ ID NO:25:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:25:

```
GGTGCTGGCG CTAACTGTG                                                  19
```

( 2 ) INFORMATION FOR SEQ ID NO:26:

( i ) SEQUENCE CHARACTERISTICS:
  ( A ) LENGTH: 20 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:26:

TGACTATTGC AGCTCCAAGG 20

( 2 ) INFORMATION FOR SEQ ID NO:27:

( i ) SEQUENCE CHARACTERISTICS:
  ( A ) LENGTH: 22 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:27:

CTTGGGTGGA GTCACATTTC TC 22

( 2 ) INFORMATION FOR SEQ ID NO:28:

( i ) SEQUENCE CHARACTERISTICS:
  ( A ) LENGTH: 22 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:28:

NGTGCCTGGC CCAAAGTACT GG 22

( 2 ) INFORMATION FOR SEQ ID NO:29:

( i ) SEQUENCE CHARACTERISTICS:
  ( A ) LENGTH: 21 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:29:

CTCTCACTGT GACATCTGCC C 21

( 2 ) INFORMATION FOR SEQ ID NO:30:

( i ) SEQUENCE CHARACTERISTICS:
  ( A ) LENGTH: 22 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:30:

NGAGTCCCCT CTCCAAAAAG CG 22

( 2 ) INFORMATION FOR SEQ ID NO:31:

( i ) SEQUENCE CHARACTERISTICS:
  ( A ) LENGTH: 20 base pairs
  ( B ) TYPE: nucleic acid
  ( C ) STRANDEDNESS: unknown ( D ) TOPOLOGY: unknown ( i i ) MOLECULE TYPE: DNA (genomic)

( x i ) SEQUENCE DESCRIPTION: SEQ ID NO:31:

CTCGTGGAAG AGGATCACCC                                                    20

( 2 ) INFORMATION FOR SEQ ID NO:32:

( i ) SEQUENCE CHARACTERISTICS:
( A ) LENGTH: 24 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:32:

NGGTGAGCGA TGTCAGACAG CTCC                                               24

( 2 ) INFORMATION FOR SEQ ID NO:33:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:33:

AGTTGTACTT CTGGGCAAGC                                                    20

( 2 ) INFORMATION FOR SEQ ID NO:34:

( i ) SEQUENCE CHARACTERISTICS:
( A ) LENGTH: 23 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:34:

NGGAGGATGG CCGCACCCTG TCC                                                23

( 2 ) INFORMATION FOR SEQ ID NO:35:

( i ) SEQUENCE CHARACTERISTICS:
( A ) LENGTH: 19 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:35:

CACAGTTAGC GCCAGCACC                                                     19

( 2 ) INFORMATION FOR SEQ ID NO:36:

( i ) SEQUENCE CHARACTERISTICS:
( A ) LENGTH: 27 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:36:

NGCCAGAAAA CTTGTTGTGA CAACAGC 27